United States Patent [19]

Østrup

[11] Patent Number: 5,460,057
[45] Date of Patent: Oct. 24, 1995

[54] METHOD AND APPARATUS FOR HANDLING SAMPLES AND SAMPLE COLLECTION SYSTEM

[75] Inventor: Jan Østrup, Kaarina, Finland

[73] Assignee: Wallac Oy, Turku, Finland

[21] Appl. No.: 90,689

[22] Filed: Jul. 13, 1993

[30] Foreign Application Priority Data

Jul. 14, 1992 [FI] Finland ................................. 923220

[51] Int. Cl.⁶ ............................. G01N 1/04; G01N 35/00
[52] U.S. Cl. ..................... 73/864.81; 422/65; 436/44; 436/46
[58] Field of Search ..................... 422/65, 66; 436/44, 436/46, 179; 73/864.81

[56] References Cited

U.S. PATENT DOCUMENTS

| | | | |
|---|---|---|---|
| 3,554,700 | 1/1971 | Maxon | 436/44 |
| 3,879,127 | 4/1975 | Storr et al. | 356/36 |
| 4,059,405 | 11/1977 | Sodickson et al. | 422/66 |
| 4,066,412 | 1/1978 | Johnson et al. | 422/65 |
| 4,144,760 | 3/1979 | Schlüeter et al. | 73/864.71 |
| 4,230,684 | 10/1980 | Pang et al. | 436/542 |
| 4,341,735 | 7/1982 | Seifried | 422/66 |
| 4,568,520 | 2/1986 | Ackerman et al. | 422/66 |
| 5,066,465 | 11/1991 | Kano et al. | 422/58 |
| 5,092,466 | 3/1992 | Anderson | 422/66 |
| 5,168,766 | 12/1992 | Stoffel | 73/864.81 |
| 5,178,834 | 1/1993 | Kagayama et al. | 422/65 |

FOREIGN PATENT DOCUMENTS

| | | | |
|---|---|---|---|
| 959392 | 12/1974 | Canada | 422/66 |
| 260136 | 3/1988 | European Pat. Off. | 422/65 |
| 39192 | 4/1978 | Japan | 422/66 |
| 144753 | 8/1983 | Japan | 422/65 |
| 1601616 | 10/1981 | United Kingdom . | |

*Primary Examiner*—Hezron E. Williams
*Assistant Examiner*—Daniel S. Larkin
*Attorney, Agent, or Firm*—Ronald J. Kubovcik

[57] ABSTRACT

Method for handling blood samples (32) wherein a blood sample is absorbed into a filter paper (30) and a sample piece (36) is taken from the filter paper from the opposite side of the absorption side. The sample piece is placed in a sample well of an uncoated micro titration plate (45) and is dissolved in a liquid so that a sample solution is formed in the well. The sample solution is transferred to a second micro titration plate (52–54) coated for the analysis. The apparatus comprises a camera (43), which identifies the filter paper (30), locates the blood sample (32), and informs the punch (47) of the location of the sample. The filter paper (30) is placed in a package, (22) having openings (25) for absorbing and punching of the sample and the covering (23) is provided with a bar code (29).

9 Claims, 6 Drawing Sheets

(PRIOR ART)

FIG.12

(PRIOR ART)

METHOD AND APPARATUS FOR HANDLING SAMPLES AND SAMPLE COLLECTION SYSTEM

The invention relates to a method and apparatus for handling samples and a sample collection system. The samples are normally blood samples.

In the method the samples are taken onto a solid substrate like filter paper, a sample piece is punched from the filter paper at a point where the blood sample has been absorbed, and the blood sample is dissolved from the sample piece to the sample solution which is conveyed to a measuring instrument for measurement. The invention also relates to an automatic sample handling apparatus for blood samples. In the sample collection system the sample is taken into a sample collection unit having a filter paper into which the sample is absorbed.

The conventional practice is to collect blood samples e.g. from newborn children onto a filter paper, dry and send them to laboratories for examination. Handling of these samples in laboratories still requires a lot of manual work. The impregnated sample piece is punched from the filter paper manually and even after that several manual operations are performed before the actual measurement of the sample is performed.

In other applications blood samples are commonly handled in liquid form. Because this kind of blood sample handling exposes the laboratory personnel to a considerable risk of infectious diseases, safety in blood sample handling has received more consideration.

Another problem is the transportation of liquid samples. Because they must sometimes be sent by post, the Post Office has made the safety regulations more stringent. Extra demands are made on bottles and packages which has considerably increased the dispatch costs. Due to these facts blood samples are more often handled so that they are not in liquid form but absorbed into some substrate like filter paper. Dried blood samples present a much smaller risk of infectious diseases than blood samples in liquid form. Sending dry blood samples by post is far easier and simpler than sending liquid packages.

However, there are drawbacks in using filter papers. Already in the stage when the sample is taken there is a problem in that there is no unified sampling system or sample collection unit. Therefore filter paper pieces of various types and sizes are used in sampling. A mere piece of filter paper is, however, flexible and difficult to handle in the sampling situation. Also the markings made on the piece of filter paper vary greatly. It is obvious that without a systematic procedure one cannot be sure that the sample can in all handling stages be linked to the right person, i.e. the donor.

A further problem is that blood analysis includes several cumbersome manual stages which are possible sources of error. The actual measuring instruments like, for example, fluorometer, luminometer, beta or gamma counter or other corresponding instruments are often automated but sample dispensing and preparation is generally still performed manually. Sample preparations stages like punching the sample piece from the filter paper, placing the punched piece into a sample vessel or the well of a sample plate, adding the buffer solution, transferring the sample vessel to the shaker, pipetting the dissolved sample into a sample vessel or into the well of the sample plate coated for the analysis are manual operations.

During the measurement, there are additional stages like adding of reagent to the sample, incubation, washing, dispensing of the measuring liquid. Normally they are also manual operations after which the sample can be placed in the actual measuring instrument.

In the applicant's DELFIA measuring method the measuring instrument is a time resolved fluorometer or TR Fluorometer which operates so that a light pulse with a wavelength of 350 nm is given to the sample in the sample well. Then follows a 400 µs wait after which light with a wavelength of 615 nm is measured for 400 µs. The measurement is repeated at a frequency of a thousand times per second.

The objective of this invention is to eliminate the above problems and to obtain a method wherein there are no manual operations on the blood samples after the sample has been taken and absorbed into a filter paper.

The method according to the invention is characterized in that the sample piece is taken from such a point of the filter paper where the blood sample has been absorbed through the filter paper, the sample piece containing the blood sample is placed in a first vessel where the blood sample is dissolved from the sample piece to the liquid so that a sample solution is formed in the vessel, the sample solution is transferred to a second vessel which is coated for the analysis and which is transferrable to a measuring instrument for measurement.

The sample solution is formed from the blood sample in such, at least partly automated process where the filter paper containing the blood sample is identified, the location of the blood sample is searched and observed, the sample piece is punched and the blood sample is dissolved in the sample liquid which is in a suitable form for feeding into the measuring instrument.

The apparatus according to the invention is characterized in that the apparatus comprises a first vessel in which the blood sample is dissolved from the sample piece to the liquid and a second vessel like a coated sample well of a micro titration plate into which the sample solution is transferred for analysis. The apparatus also comprises a detection unit which observes the location of the blood sample on the filter paper for punching the sample piece.

The sample collection system according to the invention is characterized in that the sample collection system comprises a sample collection unit which has an info part containing the information of the donor and a filter paper package for adsorbing the sample, the parts being separable from each other and provided with a same identification code like a bar code.

The sample collection unit has two parts so that the actual filter paper part has a filter paper for the samples between coverings. The covering is provided with openings through which the blood sample is dispensed onto the filter paper. The covering is also provided with a marked bar code for identification of the sample.

The second part or the info part of the sample collection unit comprises identification information in text form and the corresponding bar code as in the filter paper part. Before sample handling, these parts of the filter paper unit are separated from each other and the filter paper part goes to the sample handling apparatus of the invention.

The filter paper sample handling apparatus according to the invention comprises a feed unit from which the filter papers containing the samples are individually taken for handling. The handling apparatus further comprises a camera which first identifies the bar code and then searches the most suitable sample from the samples of the filter paper. Then the camera directs the sampling point to such a point on the filter paper where blood has well absorbed through the paper. Then the punch punches a piece from filter paper from the point determined by the camera and the piece drops into the sample well of a micro titration plate.

Buffer solution is added to the sample well containing the sample piece and the micro titration plate containing the sample is transferred to the shaker. The shaken sample is transferred to a pipetting unit which pipets the sample solution dissolved from the filter paper into one or more coated micro titration plates. The plates are transferred further to a measuring instrument which is provided with a fluorometer, for example.

Measurement of the samples can be performed with several different methods depending on which kind of material the wells of the micro titration plates going into the measuring instrument are coated with and which kinds of reagent liquids are used. In the applicant's DELFIA method the following analyses can be used, for example, TSH=Thyroid Stimulating Hormone IRT=Immuno Reactive Trypsine 17α-OHP=17α-OH-Progesterone or CK=Creating Kinase.

Each of these analyses can be performed if the sample is placed in a sample well which has a coating suitable for the particular analysis and a reagent is added which is suitable for the analysis. Thus one label can be measured from each sample well.

According to a current method, one piece of filter paper or disk usually with a diameter of 3 mm, is needed for each analysis. Thus a substantial amount of blood is needed to absorb a sufficiently large blood spot. Several, three or four, disks must be obtained from this blood spot because one disk is used for only one analysis.

From each disk, 200 µl of sample is dissolved for the measurement. This is a fairly large quantity for only a single analysis. The whole quantity is used in the analysis. On the other hand, it is also a problem that the filter paper disks have not always taken from such a point where the whole disk would be sufficiently saturated with the sample. In this case, the concentration of the 200 µl solution may remain so small that a sufficiently reliable measuring result cannot be obtained. Variations in the liquid concentration causes at least a considerable unevenness in the quality of the results.

It is also possible that the coatings of the sample wells suit many different analyses. In this case the analysis can be selected by changing the label. Furthermore, it is possible that the coating of the sample well and the reagent liquid are multi-functional so that several different labels can be measured from a single sample well.

According to the invention, the sample disk has a diameter of 5 mm so that the area of the disk is nearly threefold compared to those used previously with a diameter of 3 mm. According to the invention, the sample disk is taken from the center of the sample or from such a point that is completely saturated with the blood sample. When a 200 µl sample is dissolved from this kind of disk the concentration is certainly high enough for a reliable analysis.

According to the invention, the sample solution is divided into two or more parts, in the exemplary embodiment in three parts, which are each pipetted on a different sample plate. If one measures, e.g., four labels from a single sample well of the sample plate, it means that from one disk one can measure 12 analyses. It is obvious that the blood sample is used in a much more efficient and versatile way. There is also an advantage that there is no need to take as much blood as before. However, the number of obtained analyses is higher. Some of the samples, which were simultaneously taken, on the filter paper are saved for later control analyses.

The invention is described in the following by means of examples with reference to the enclosed drawings in which.

Figure 1:
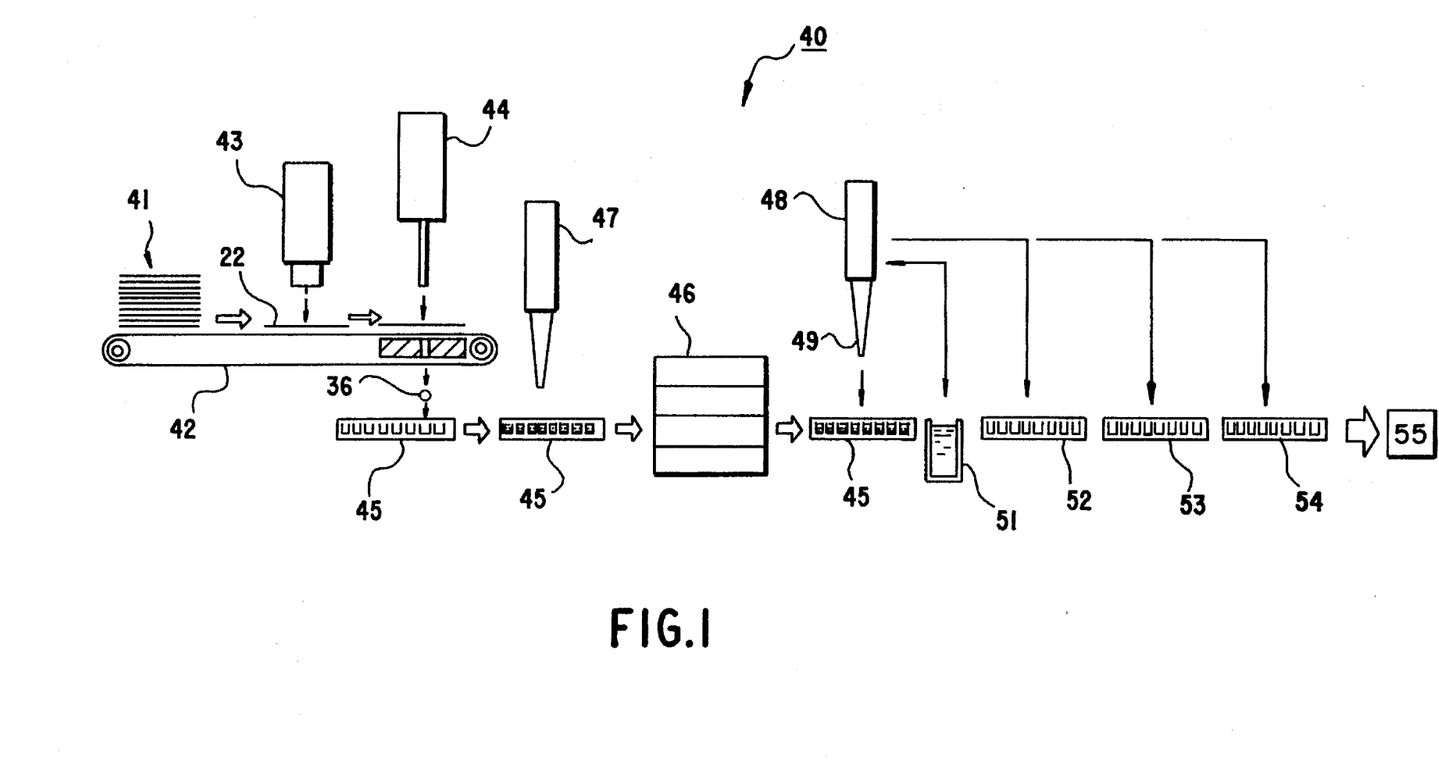
FIG. 1 shows schematically an apparatus according to the invention for handling samples absorbed into filter paper seen from the side.

FIG. 1 shows schematically a side view of the apparatus 40 of the invention for handling blood samples for analysis. The samples have been absorbed into filter paper so that they are dry and easy to handle. Therefore, the personnel operating the apparatus are not at risk to infection even though the samples might contain infectious diseases.

The manageability of the samples has been achieved by placing the actual filter paper part into a protected filter paper package 22 where the filter paper is inside a twofold covering. The covering of the filter paper package 22 has openings through which the blood sample is absorbed into the filter paper inside. It is also through these openings that the pieces or disks are punched from the filter papers during sample handling from which pieces the sample is then dissolved for the measurement. The structure of the filter paper package 22 is shown in more detail in FIG. 3–7.

In the sample handling apparatus 40 of FIG. 1, the filter paper packages 22 are placed in store 41 wherefrom the apparatus fetches them individually. FIG. 1 shows how a filter paper packages are individually moved by a conveyor 42. The conveyor 42 first moves the handled filter paper package 22 opposite to the camera 43 which identifies the sample from the bar code on the covering of the filter paper package 22. The filter paper package 22 is moved under the camera 43 also sideways whereby the camera 43 investigates through the openings of the filter paper package 22 all blood samples absorbed into the filter paper. As a result of the investigation the camera 43 determines the best sample and stores the coordinates in memory.

After the camera 43, the filter paper package 22 moves to the punch 44 under which an empty and uncovered micro titration plate 45 has been simultaneously transferred from the shaker 46. The punch punches out through the opening of the covering of the filter paper package 22 a piece or disk from the filter paper inside at a location indicated by the camera 43. This piece is taken from a point of the filter paper which is best saturated with the blood sample. The punched piece of filter paper 36 drops to the sample well of the underlying micro titration plate 45. If unpunched samples remain in the filter paper package 22, the filter paper package 22 can be stored for later investigation.

Empty micro titration plates 45 are stored in the shaker 46, which can accommodate four micro titration plates 45. The micro titration plates 45 are fetched individually from the shaker 46 to under the punch 44. In the punch station 44, the micro titration plate 45 is moved both forwards and sideways so that each sample well comes in turn under the punch 44. When all sample wells of the micro titration plate 45 have received a punched piece of filter paper 36, the micro titration plate 45 moves to a position 47 where buffer solution is added. There the micro titration plate 45 is again moved both forwards and sideways so that each sample well comes in turn under the pipette 47 dispensing the buffer solution.

When each sample well has received the buffer solution, the micro titration plate 45 moves back to the shaker 46. When all four shelves of the shaker 46 become occupied with micro titration plates 45 with the sample pieces and the buffer solution, the samples are shaken.

After shaking, the micro titration plates 45 are individually moved to the pipetting station 48 with twelve adjacent pipettes. In the pipetting station 48, sample solution dissolved from the filter paper piece is aspirated from a micro titration plate 45 and moved to coated micro titration plates 52–54 of the pipette. Uncoated micro titration plates 45 are disposable and they are thrown away after use.

The pipetting station 48 also comprises a rinsing basin 51 where pipette tips 49 are rinsed before pipetting the next sample. When the sample solution has been transferred to the coated sample wells of the micro titration plates 52–54, the micro titration plates 52–54 are further transferred to the actual measuring instrument where, among other things, necessary reagents are added to the sample wells. The measuring instrument e.g. a fluorometer is shown in FIG. 1 as analytical instrument 55.

Figure 2:
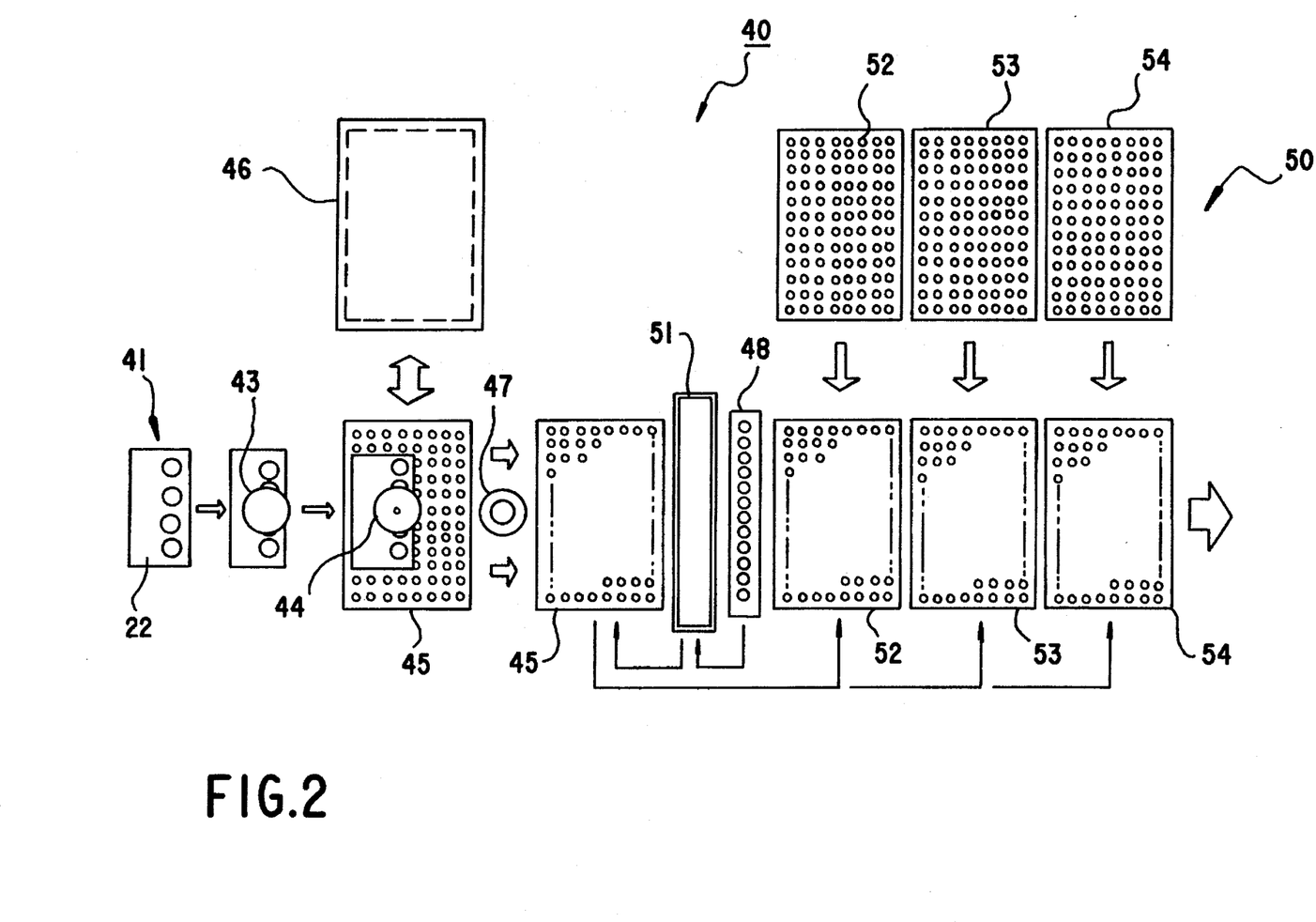
FIG. 2 shows the apparatus of FIG. 1 seen from above.

FIG. 2 shows from above the disposition of the devices of the sample handling apparatus 40 of FIG. 1. The filter paper packages 22 containing the filter papers onto which the blood samples have been absorbed are moved individually from the store 41 to the camera 43, which identifies the sample from the bar code of the covering of the filter paper package 22. Then the filter paper package 22 is moved under the camera 43 also sideways whereby the camera 43 explores through the openings of the filter paper package 22 all blood samples absorbed into the filter paper and indicates the best sample and stores its coordinates in memory.

In the punch station 44, the best blood sample indicated by the camera 43 is moved under the punch 44. At the same time, an empty and uncoated micro titration plate 45 has been fetched from the shaker 46 under the punch, the micro titration plate having 8×12 sample wells or ninety six wells altogether. The micro titration plate 45 is moved one step at a time in the punch station 44 so that each sample well comes in turn underneath the punch 44.

When each sample well of the micro titration plate 45 has received a punched piece of filter paper, the micro titration plate 45 moves to a station 47 for dispensing the buffer solution. There, the micro titration plate 45 is moved one step at a time so that each sample well comes in turn under the pipette 46 dispensing the buffer solution. After dispensing of the buffer solution the micro titration plate 45 moves to the shaker 46.

The micro titration plate 45 moves from the shaker 46 to the pipetting station 48 where the sample solution dissolved from the sample piece is transferred to coated micro titration plates 52–54 for the analysis. The pipetting station 48 comprises twelve pipettes which pipette from a row of uncoated sample wells of the micro titration plate 45, i.e., twelve samples at a time to the sample wells of coated micro titration plates 52–54. Since each pipette always stands at one row of sample wells, neither the micro titration plate 45 nor the pipettes of pipetting station 48 need to move sideways. After each pipetting the tips of the pipettes 48 are rinsed in the rinsing basin 51.

Micro titration plates 52–54 coated for the analysis are stored in a plate store 50 having twelve micro titration plates with three plates lying side by side and four plates on top of the other. Three micro titration plates 52–54 are moved at a time to the pipetting unit 48 as shown in FIG. 2.

In the exemplary case of FIGS. 1 and 2, the sample solution aspirated in the pipetting unit 48 from the sample well of an uncoated micro titration plate 45 is divided into three parts. One part is conveyed to the sample well of the micro titration plate 52, the second part to the well of the micro titration plate 53 and the third part to the well of the micro titration plate 54. The sample wells of these micro titration plates 52–54 have been coated, for example, so that the micro titration plate 52 is used for TSH or Thyroid Stimulating Hormone analysis, micro titration plate 53 is used for IRT or Immuno Reactive Trypsine analysis and the micro titration plate 54 is used for $17\alpha$-OHP=$17\alpha$-OH-Progesterone analysis.

In this way, from the four uncoated micro titration plates 45 of the shaker 46 of the sample handling apparatus 40 the sample solution is obtained to the twelve coated micro titration plates 52–54. The number twelve has been chosen in this example because the shaker incubator in the fluorometer measuring instrument utilizing the applicant's Delfia-method can take this number of coated micro titration plates 52–54. The actual measuring instrument is not shown in FIG. 2.

Figure 3:
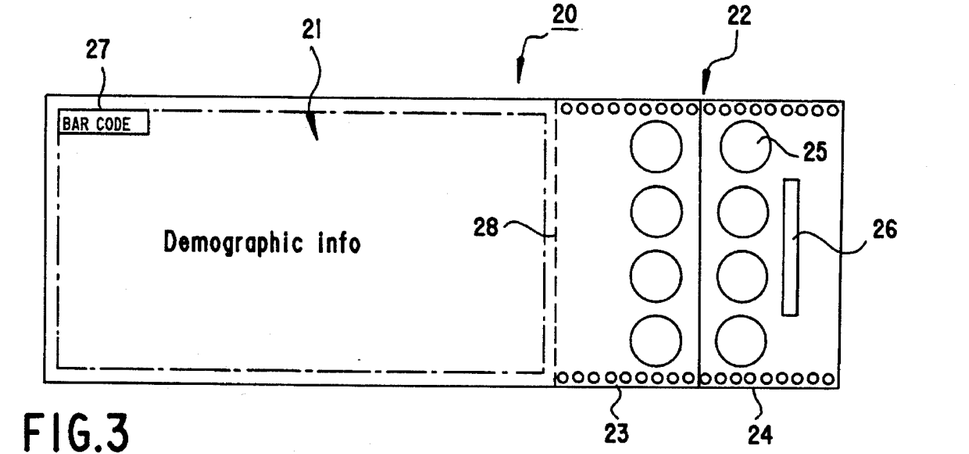
FIG. 3 shows the plain covering of the filter paper unit.

FIG. 3 shows a plain covering of the sample collection unit 20 from above. The sample collection unit 20 comprises two primary parts which are the info part 21 and the filter paper package 22, which parts can be separated from each other by tearing along the tear line 28. The personal data of the donor is marked in the info part 21. The actual sample is absorbed into the filter paper package 22.

The covering of the filter paper package 22 is twofold so that the filter paper into which the blood samples are absorbed is placed between the parts 23 and 24 of the covering which are folded on top of the other. Both halves 23 and 24 contain openings 25 for conducting the blood sample through the opening onto the filter paper. In addition to these openings, the covering is provided with an elongated opening 26 for reading markings of quality, etc., printed on the filter paper which is to be placed inside the covering. As a check, the info part 21 of the sample collection unit 20 has a bar code 27 marked in the corner of the info part 21.

Figure 4:
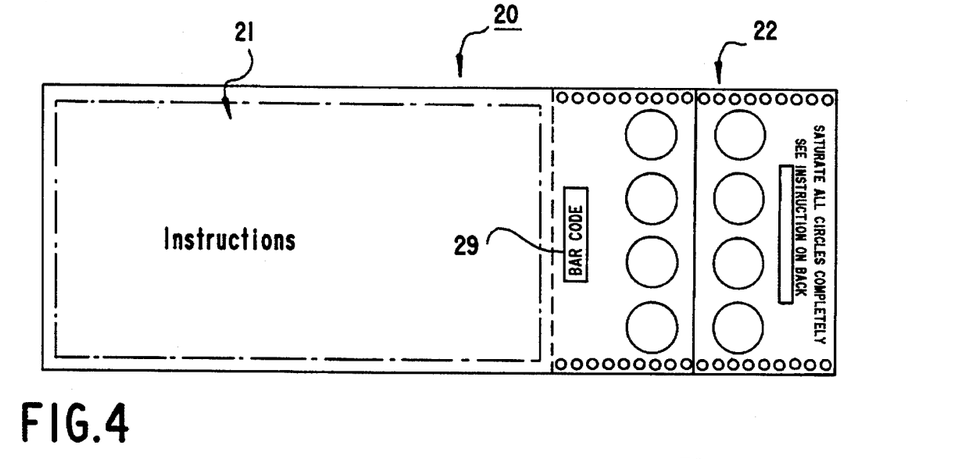
FIG. 4 shows the opposite side of the covering of the filter paper unit of FIG. 3.

FIG. 4 shows the opposite side of the covering of the sample collection unit 20 of FIG. 2. As seen in FIG. 4, the opposite side of the info part contains instructions. There are instructions printed on the surface of the filter paper package 22 and the same bar code 29 as on the other side of the info part.

Figure 5:
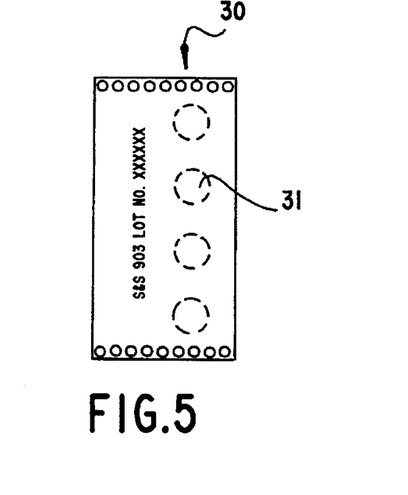
FIG. 5 shows the filter paper of the filter paper unit.

FIG. 5 shows the filter paper 30 which is placed inside the filter paper package 22 of the sample collection unit 20. It may have printed information of quality and four circles 31 printed with dashed lines showing the places onto which the drops of sample blood are applied.

Figure 6:
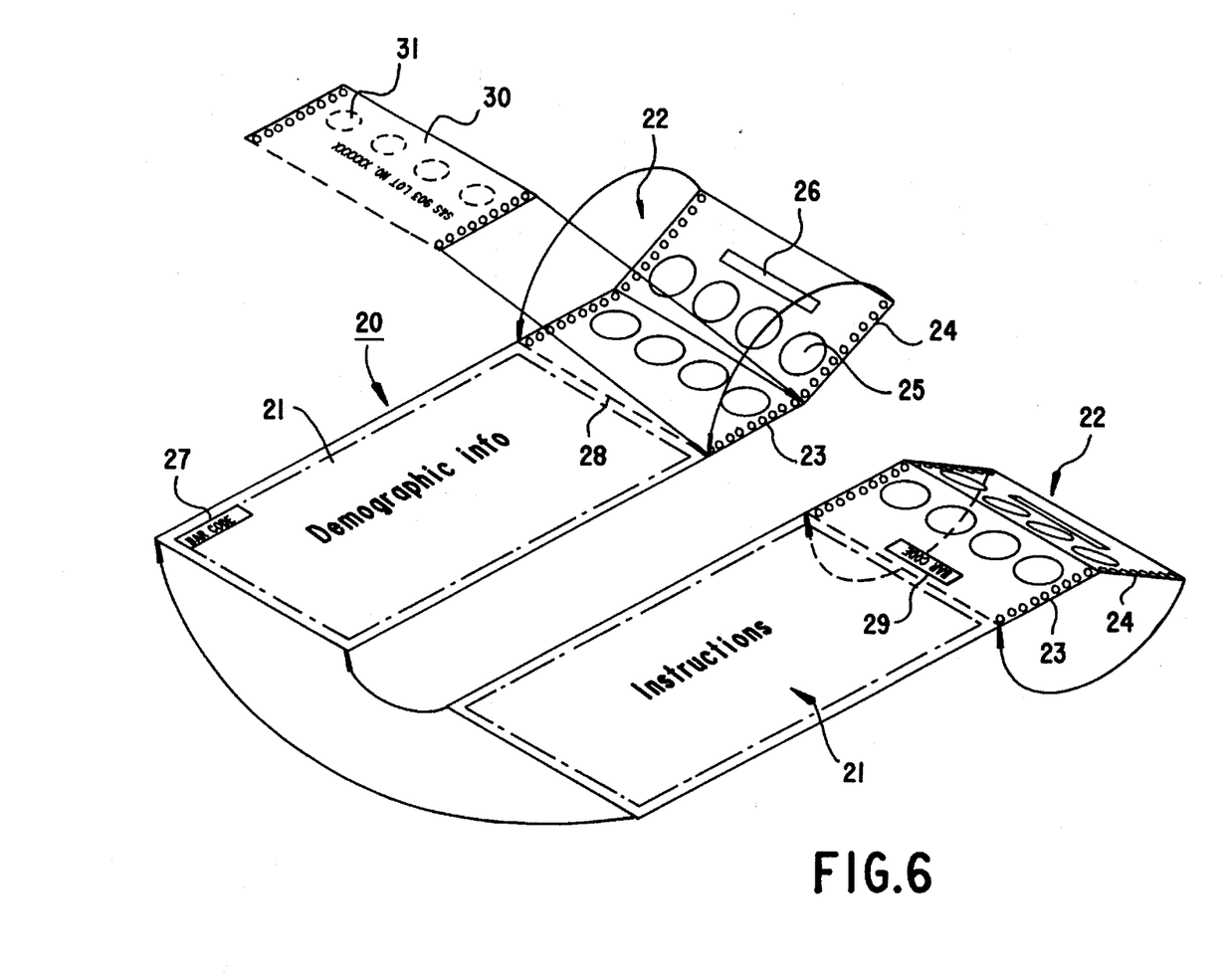
FIG. 6 shows the assembly of the filter paper unit according to the invention.

FIG. 6 shows the assembly of the collection unit 20 of the invention. The assembly is already done in the manufacturing plant but FIG. 6 clearly shows the structure of the sample collection unit 20. In the assembly stage, part 24 of the filter paper package 22 is folded over part 23 and the filter paper 30 is placed in between. In this way the filter paper 30 remains inside the covering so that only part of the filter paper is visible through the openings 25 and 26.

Figure 7:
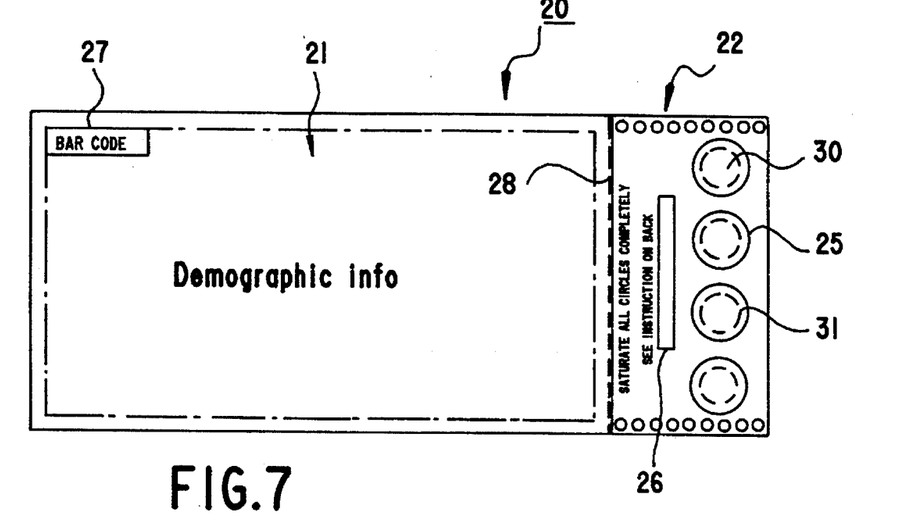
FIG. 7 shows an assembled filter paper unit.

FIG. 7 shows a complete sample collection unit 20 comprising the info part 21 and the filter paper package 22 in which the actual filter paper 30 is between the halves of the covering. The filter paper 30 is visible only through the openings 25 and 26. Drops of blood samples are applied to the circles 31 on the filter paper 30. When samples have been dispensed to all openings 25, the filter paper package 22 is separated from the info part along the tear line 28.

Figure 8:
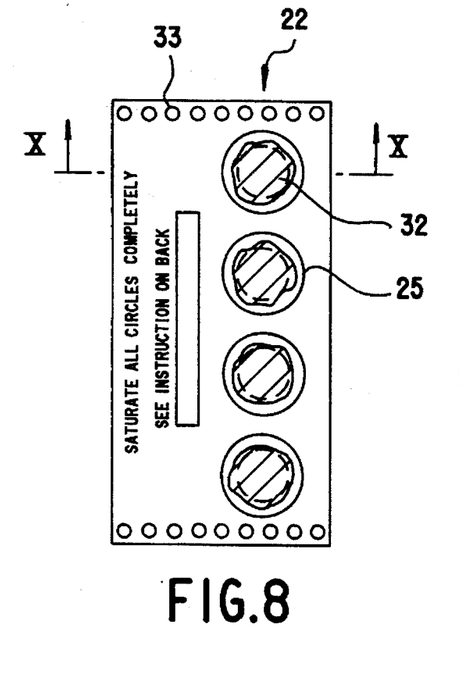
FIG. 8 shows the filter paper unit after the blood samples have been dispensed onto the filter paper through the openings.

FIG. 8 shows a filter paper package 22 in which the blood samples 32 have been applied through the openings 25 onto the filter paper 30 inside the package. As seen from FIG. 8, the blood drop has spread well on the filter paper 30 even outside the line 31. Hence it can be assumed that there is enough sample on the filter paper 30 in each sample position 31.

The filter paper package 22 of FIG. 8 is provided with perforations 33 at both edges to facilitate moving of the filter paper package 22 in the automatic sample handling apparatus.

Figure 9:
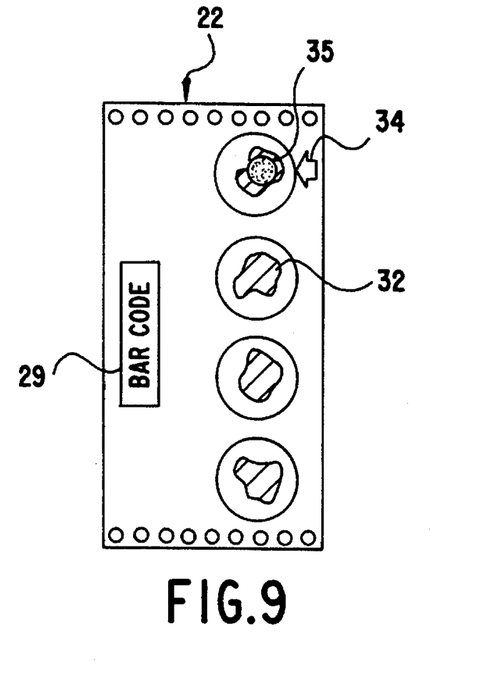
FIG. 9 shows the opposite side of the filter paper part of FIG. 8.

FIG. 9 shows the opposite side of the filter paper package 22 of FIG. 8. As seen from FIG. 9 the sample is not everywhere absorbed through the filter paper 30, although the blood drops in FIG. 8 were well spread even outside the marked circle 31. However, there should be so much of the sample absorbed into the filter paper 30 that a sufficient amount of dissolved sample solution could be obtained for the measurement.

Therefore, the bar code 29 of the filter paper package 22 is arranged on this side which is opposite to the side onto which the blood sample is fed. The purpose of this arrangement is that the identification of the filter paper package 22 can take place only from that side which is simultaneously used for checking that a sufficient amount of sample has been absorbed into the filter paper 30 inside the filter paper package 22.

As seen in FIG. 9, each blood sample 32 is different in shape seen from this side and considerably smaller than on the opposite side. This means that the blood sample has absorbed through only at those points where the filter paper 30 of the filter paper package 22 has been stained as seen from this side. This is important because then the punch can take such a point from the filter paper 30 where the examined blood sample has absorbed through.

Absorption of the blood sample can also be inspected visually and, at the same, a mark 34 put on the covering of the filter paper package 22 telling the location of an acceptable sample. The apparatus of the invention is provided with a camera which first reads the bar code 29 and identifies the mark 34 based on visual examination, if there is such a mark. The camera is, however, capable of finding the optimum point 35 for punching without the mark 34 based on visual examination.

Figure 10:
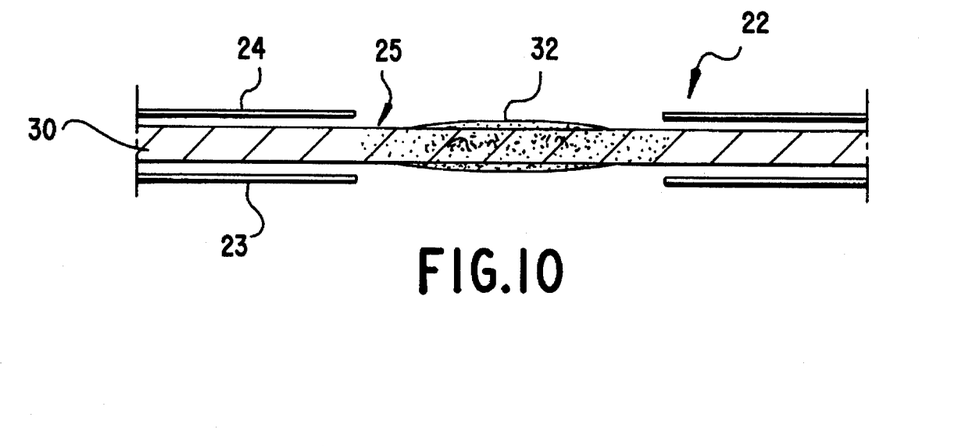
FIG. 10 shows the cross-section along the line X—X of FIG. 8.

FIG. 10 shows a cross-section of FIG. 8 showing the structure of the filter paper package 22 of the invention. The actual filter paper 30 is placed between the protective covering papers 23 and 24 which are provided with openings 25. The blood sample is absorbed into the filter paper 30 through the opening 25 and the sample piece or disk is punched from the filter paper 30 through the same opening. This kind of structure protects well the actual filter paper 30 while the structure is rigid enough so that the filter paper package 22 can be readily handled in the sampling situation.

Figure 11:
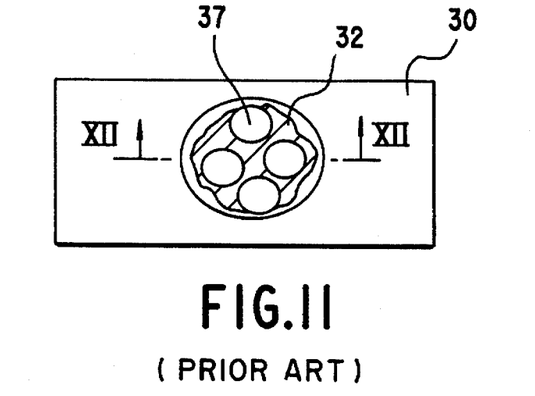
FIG. 11 shows a punched filter paper of prior art.

In FIG. 10, a blood sample 32 has been absorbed into the filter paper 30 so that the filter paper has slightly swollen at the point. Swelling of the the filter paper 30 is slightly exaggerated in FIG. 10 for clarity. However, the figure shows that the point of the blood sample 32 is protected by the protective covering papers 23 and 24 so that the sample cannot touch another sample nor the bottom even if the filter paper packages 22 were stacked on top of each other. FIG. 11 shows for comparison a known practice for taking a blood sample 32 by means of a filter paper 30. Several disks are punched from the filter paper by the sample 32 leaving holes 37 in the filter paper 30. Seen from the surface it would seem as if sampling had succeeded and all sample disks have been taken from a place of the filter paper 30 into which the blood sample had absorbed well.

Figure 12:
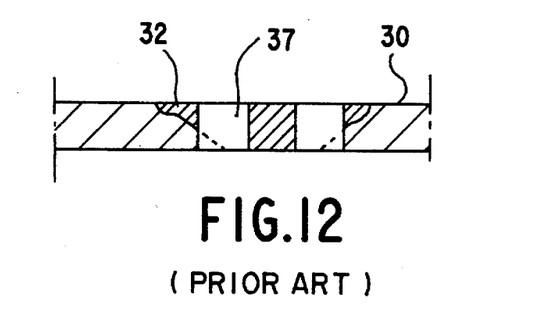
FIG. 12 shows the cross-section along the line XII—XII of FIG. 11.

In FIG. 12, the blood sample 32 absorbed into the filter paper 30 has not absorbed through by the edges of the sample. Hence by mistake, the sample disks have been taken from places of the filter paper 30 where the sample disks contain only partly the sample. It is obvious that when a sample is dissolved from this kind of sample disk, one obtains a sample solution with too low a concentration to get a reliable measuring result. The result is further impaired by the fact that, in a filter paper 30, the blood sample 32 absorbs from the center towards the edges wherefore the sample concentration at the edges is less than in the center.

There is a clear difference between the known method and that of the invention when FIGS. 9 and 11 are compared. In the known method, according to FIG. 11, several samples are taken some of which inevitably are located near the edges where one cannot be sure whether the filter paper is saturated through or not. According to the invention, as shown in FIG. 9, the sample disk is taken from the opposite side, i.e, the worse side of the filter paper 30 where a visible sample 32 means that it has certainly absorbed through the filter paper. In addition, the sample disk is taken from the center of the blood sample 32 from the best possible place.

It is obvious to a specialist in the field that different embodiments of the invention can vary within the limits of the following claims.

I claim:

1. Method for handling blood samples according to which method a blood sample is absorbed into a substrate, a sample piece is taken from the substrate at a point where the blood sample has been absorbed, the sample piece is placed in a vessel, and the sample is dissolved in the vessel in a liquid so that a sample solution is formed in the vessel, characterized in that the sample piece is taken from such a point of the substrate where the blood sample has absorbed through the substrate, the sample piece containing the blood sample is placed in a first vessel where the blood sample is dissolved from the sample piece to the liquid so that a sample solution is formed in the vessel, and the sample solution is transferred to a second vessel which is coated for an analysis and which is transferrable to a measuring instrument for measurement, and wherein the location of the sample piece to be taken from the substrate is determined by observing the substrate from the opposite side of the side from which the blood sample has absorbed into the substrate.

2. Method according to claim 1 characterized in that the sample solution formed in the first vessel is divided into at least two portions which are transferred to at least two second vessels which are coated for an analysis.

3. Method according to claim 2 characterized in that the sample solution formed in the first vessel is divided and transferred to at least two separate second vessels, to sample wells which are coated for the analysis.

4. Method according to claim 3 characterized in that the sample solution formed in the sample well of a first vessel is divided and transferred by pipetting to at least two different second vessels, to sample wells which are coated for different analyses so that at least two different analyses are obtained from the same sample solution.

5. Method according to any one of claims 1, 2, 3 or 4, characterized in that the substrate is identified, the location of the sample piece to be taken therefrom is determined and the sample is dissolved and transferred to a vessel coated for the analysis in a process which is at least partly automated.

6. Apparatus comprising a device for taking a sample piece from a point of the substrate onto which a blood sample has been absorbed, and a vessel where the blood sample is dissolved from the sample piece to a liquid so that a sample solution is formed in the vessel characterized in that the apparatus comprises a first vessel in which the blood sample is dissolved from the sample piece to the liquid, and a second vessel into which the sample solution is transferred for an analysis, wherein the apparatus further comprises a detection unit for detecting the location of the blood sample on the substrate from the opposite side of the side from which the blood sample has been absorbed.

7. Apparatus according to claim 6 characterized in that the apparatus comprises a detection unit which identifies a code of the substrate from the opposite side of the absorption side of the blood sample.

8. Apparatus according to claim 6 characterized in that the apparatus comprises a camera which identifies the substrate, locates the blood sample and informs the device for taking the sample piece of the location of the sample.

9. Apparatus comprising a device for taking a sample piece from a point of the substrate onto which the blood sample has been absorbed, and a vessel where the blood sample is dissolved from the sample piece to a liquid so that a sample solution is formed in the vessel, characterized in that the apparatus comprises a first vessel in which the blood sample is dissolved from the sample piece to the liquid, and a second vessel into which the sample solution is transferred for an analysis, wherein the apparatus comprises a shaker, which functions as a storage means for the vessel in which the sample piece is dissolved, and a plate storage means where coated vessels for an analysis are situated.

* * * * *